(12) United States Patent
Weiblen et al.

(10) Patent No.: US 9,297,791 B2
(45) Date of Patent: Mar. 29, 2016

(54) GAS SENSOR WITH THERMAL SHOCK PROTECTION

(71) Applicant: Robert Bosch GmbH, Stuttgart (DE)

(72) Inventors: Hannes Weiblen, Metzingen (DE); Craig Magera, Simpsonville, SC (US); Karen Carwile, Anderson, SC (US); John Day, Greenville, SC (US)

(73) Assignee: Robert Bosch GmbH, Stuttgart (DE)

( * ) Notice: Subject to any disclaimer, the term of this patent is extended or adjusted under 35 U.S.C. 154(b) by 321 days.

(21) Appl. No.: 13/835,543

(22) Filed: Mar. 15, 2013

(65) Prior Publication Data
US 2014/0174177 A1 Jun. 26, 2014

Related U.S. Application Data

(60) Provisional application No. 61/740,199, filed on Dec. 20, 2012.

(51) Int. Cl.
*G01L 5/16* (2006.01)
*G01N 33/00* (2006.01)
*G01N 27/407* (2006.01)

(52) U.S. Cl.
CPC ........ *G01N 33/0009* (2013.01); *G01N 27/4077* (2013.01)

(58) Field of Classification Search
CPC ........................................ G01L 5/16
USPC .......................................... 73/431
See application file for complete search history.

(56) References Cited

U.S. PATENT DOCUMENTS

| 4,199,425 | A | 4/1980 | Sinkevitch |
| 4,217,470 | A | 8/1980 | Kirner |
| 4,257,863 | A | 3/1981 | Hoffman |

(Continued)

FOREIGN PATENT DOCUMENTS

| DE | 4342064 | 6/1994 |
| DE | 102005020792 | 11/2006 |

(Continued)

OTHER PUBLICATIONS

"3M Nextel™ Ceramic Textiles Technical Notebook", dated Nov. 2004, 3M Ceramic Textiles and Composites, St. Paul, MN, http://www.3m.com/market/industrial/ceramics/pdfs/Nextel_Tech_Notebook_11.04.pdf, Statement of Relevance attached.

(Continued)

*Primary Examiner* — Lisa Caputo
*Assistant Examiner* — Jamel Williams
(74) *Attorney, Agent, or Firm* — Michael Best & Friedrich LLP

(57) ABSTRACT

A gas sensor includes a sensor housing, and a sensing element located within the sensor housing, the sensing element defining an axis and having a distal end extending from the sensor housing. The gas sensor further includes a sensor protection element coupled to the sensor housing and at least partially surrounding the distal end of the sensing element. The sensor protection element includes a tube, the distal end of the sensing element located within the tube, the tube including a window located along a side of the tube adjacent the distal end of the sensing element. The sensor protection element further includes a fabric layer positioned adjacent the window, the fabric layer spaced from the sensing element and extending generally parallel to the axis.

19 Claims, 6 Drawing Sheets

(56) References Cited

U.S. PATENT DOCUMENTS

| | | | |
|---|---|---|---|
| 4,272,349 A | 6/1981 | Furutani et al. | |
| 4,279,666 A | 7/1981 | Micheli | |
| 4,283,261 A | 8/1981 | Maurer et al. | |
| 4,296,148 A | 10/1981 | Friese | |
| 4,331,632 A | 5/1982 | Galloway | |
| 4,356,065 A | 10/1982 | Dietz | |
| 4,402,821 A | 9/1983 | Yan | |
| 4,409,127 A | 10/1983 | Keppel et al. | |
| 4,478,067 A | 10/1984 | Ohta et al. | |
| 4,500,412 A | 2/1985 | Takahashi et al. | |
| 4,502,939 A | 3/1985 | Holfelder et al. | |
| 4,535,316 A | 8/1985 | Wertheimer et al. | |
| 4,548,442 A | 10/1985 | Sugden et al. | |
| 4,584,086 A | 4/1986 | Hayakawa et al. | |
| 4,655,892 A | 4/1987 | Satla et al. | |
| 4,828,807 A | 5/1989 | Domesle et al. | |
| 4,851,105 A | 7/1989 | Ishiguro et al. | |
| 4,859,307 A | 8/1989 | Nishizawa et al. | |
| 4,863,583 A | 9/1989 | Kurachi et al. | |
| 4,985,126 A | 1/1991 | Haefele et al. | |
| 4,995,256 A | 2/1991 | Norlien et al. | |
| 5,006,221 A | 4/1991 | Uchikawa et al. | |
| 5,160,598 A | 11/1992 | Sawada et al. | |
| 5,169,513 A | 12/1992 | Mase et al. | |
| 5,174,885 A | 12/1992 | Hayakawa et al. | |
| 5,268,086 A | 12/1993 | Hamburg et al. | |
| 5,271,816 A | 12/1993 | Tanaka et al. | |
| 5,271,821 A | 12/1993 | Ogasawara et al. | |
| 5,302,276 A | 4/1994 | Kato et al. | |
| 5,310,575 A | 5/1994 | Friese et al. | |
| 5,368,713 A | 11/1994 | Friese et al. | |
| 5,380,424 A | 1/1995 | Friese et al. | |
| 5,389,340 A | 2/1995 | Satake | |
| 5,419,828 A | 5/1995 | Nakano et al. | |
| 5,435,901 A | 7/1995 | Friese et al. | |
| 5,443,711 A | 8/1995 | Kojima et al. | |
| 5,486,279 A | 1/1996 | Friese et al. | |
| 5,492,612 A | 2/1996 | Kennard, III et al. | |
| 5,507,937 A | 4/1996 | Renz et al. | |
| 5,593,558 A | 1/1997 | Sugino et al. | |
| 5,685,964 A | 11/1997 | Watanabe et al. | |
| 5,766,434 A | 6/1998 | Fujii et al. | |
| 5,773,894 A | 6/1998 | Friese et al. | |
| 5,814,285 A | 9/1998 | Kojima et al. | |
| 5,849,165 A | 12/1998 | Kojima et al. | |
| 5,849,660 A | 12/1998 | Takemoto et al. | |
| 5,925,814 A | 7/1999 | Tsuzuki et al. | |
| 5,948,225 A | 9/1999 | Katafuchi et al. | |
| 5,997,707 A | 12/1999 | Kato et al. | |
| 6,007,688 A | 12/1999 | Kojima et al. | |
| 6,068,746 A | 5/2000 | Kojima et al. | |
| 6,164,120 A | 12/2000 | Friese et al. | |
| 6,184,416 B1 | 2/2001 | Ding et al. | |
| 6,203,678 B1 | 3/2001 | Leonhard et al. | |
| 6,319,376 B1 | 11/2001 | Graser et al. | |
| 6,350,357 B1 | 2/2002 | Wiedenmann et al. | |
| 6,358,383 B2 | 3/2002 | Nelson et al. | |
| 6,408,680 B2 | 6/2002 | Friese et al. | |
| 6,409,899 B1 | 6/2002 | Satou et al. | |
| 6,453,723 B1 | 9/2002 | Ichikawa et al. | |
| 6,544,405 B2 | 4/2003 | Clyde et al. | |
| 6,630,062 B1 | 10/2003 | Anderson et al. | |
| 6,637,256 B2 | 10/2003 | Shirai | |
| 6,660,145 B2 | 12/2003 | Hotta et al. | |
| 6,672,137 B1 | 1/2004 | Isomura et al. | |
| 6,777,370 B2 | 8/2004 | Chen | |
| 6,824,661 B2 | 11/2004 | Lawless | |
| 7,211,180 B2 | 5/2007 | Schneider | |
| 7,212,993 B1 | 5/2007 | Bodurtha et al. | |
| 7,329,844 B2 | 2/2008 | Kojima et al. | |
| 7,493,796 B2 | 2/2009 | Wilde | |
| 7,537,383 B2 | 5/2009 | Althöfer et al. | |
| 8,132,444 B2 | 3/2012 | Cloutier et al. | |
| 2001/0035045 A1 | 11/2001 | Hibino et al. | |
| 2001/0045120 A1 | 11/2001 | Friese et al. | |
| 2002/0046947 A1 | 4/2002 | Lawless | |
| 2002/0102347 A1 | 8/2002 | Clyde et al. | |
| 2002/0103078 A1 | 8/2002 | Hu et al. | |
| 2003/0115130 A1 | 6/2003 | Stump | |
| 2004/0040843 A1 | 3/2004 | Weyl et al. | |
| 2004/0154920 A1 | 8/2004 | Schneider et al. | |
| 2005/0224347 A1* | 10/2005 | Hahn et al. | 204/424 |
| 2005/0234797 A1 | 10/2005 | Schwartz | |
| 2006/0226009 A1 | 10/2006 | Schneider et al. | |
| 2007/0170057 A1 | 7/2007 | Kobayashi et al. | |
| 2007/0208650 A1 | 9/2007 | McGill et al. | |
| 2007/0215469 A1 | 9/2007 | Imamura | |
| 2007/0244780 A1 | 10/2007 | Liu | |
| 2007/0246360 A1 | 10/2007 | Schneider et al. | |
| 2007/0277590 A1 | 12/2007 | Wilde | |
| 2008/0022754 A1* | 1/2008 | Nakagawa | 73/31.05 |
| 2008/0223110 A1 | 9/2008 | Weyl et al. | |
| 2008/0274559 A1 | 11/2008 | Fleischer et al. | |
| 2008/0293557 A1 | 11/2008 | Schofalvi et al. | |
| 2009/0020424 A1 | 1/2009 | Schneider et al. | |
| 2009/0101502 A1 | 4/2009 | Waldrop et al. | |
| 2009/0255812 A1 | 10/2009 | Yoshida et al. | |
| 2010/0155240 A1 | 6/2010 | Matsuoka et al. | |
| 2010/0163411 A1 | 7/2010 | Su et al. | |
| 2010/0242574 A1 | 9/2010 | Cloutier et al. | |
| 2010/0264026 A1 | 10/2010 | Schneider et al. | |
| 2013/0031952 A1 | 2/2013 | Day et al. | |

FOREIGN PATENT DOCUMENTS

| | | | |
|---|---|---|---|
| EP | 0520528 | 12/1992 | |
| EP | 1125488 | 8/2001 | |
| EP | 1231464 | 8/2002 | |
| EP | 1231464 A1 * | 8/2002 | G01N 27/407 |
| JP | 61079155 | 4/1986 | |
| JP | 61207961 | 9/1986 | |
| JP | 2002054554 | 10/2002 | |
| WO | 8904480 | 5/1989 | |
| WO | 0134951 | 5/2001 | |
| WO | 0167082 | 9/2001 | |
| WO | WO 03104791 A1 * | 12/2003 | G01N 27/407 |
| WO | 2005090956 | 9/2005 | |
| WO | 2005121761 | 12/2005 | |
| WO | 2005121763 | 12/2005 | |
| WO | 2008151054 | 12/2008 | |
| WO | 2009006290 | 1/2009 | |

OTHER PUBLICATIONS

Admitted Prior Art—"Micro & Nano Porous Ceramics", Ceramatec, Inc., Salt Lake City, UT, http://www.ceramatec.com/technology/other-ceramic-technologies/micro-&-nano-porous-ceramics/index.php, Statement of Relevance attached.

Admitted Prior Art—"Rescor Castable Ceramics", Cotronics Corporation, Brooklyn, NY, http://www.cotronics.com/vo/cotr/pdf/onepg700.pdf, Statement of Relevance attached.

Admitted Prior Art—"RESBOND™ 919", Cotronics Corporation, Brooklyn, NY, http://www.cotronics.com/vo/cotr/pdf/919%20NP.pdf, Statement of Relevance attached.

Micaver HT product brochure, Saint-Gobain Quartz, Jan. 2004, 2 pages.

Written Opinion for International Appl. No. PCT/US2013/075334 dated Mar. 25, 2014, 8 pages.

Search Report for International Appl. No. PCT/US2013/075334 dated Mar. 25, 2014, 5 pages.

* cited by examiner

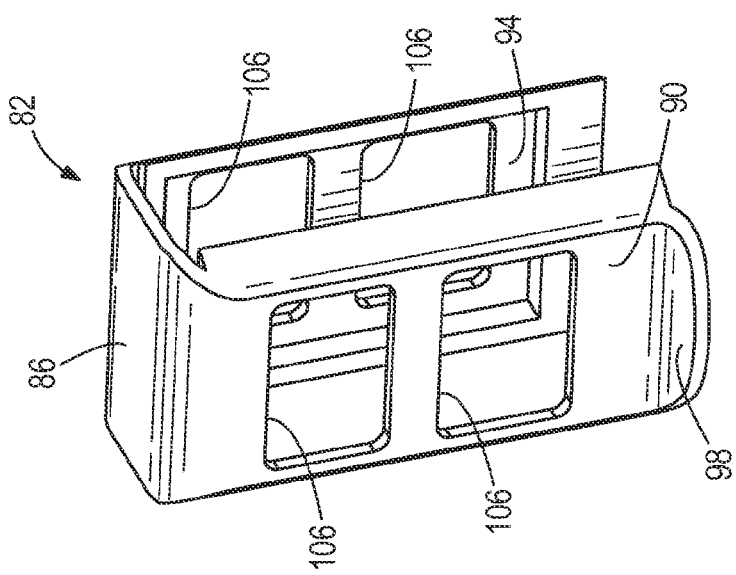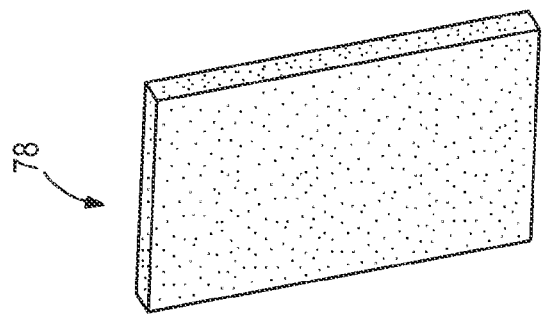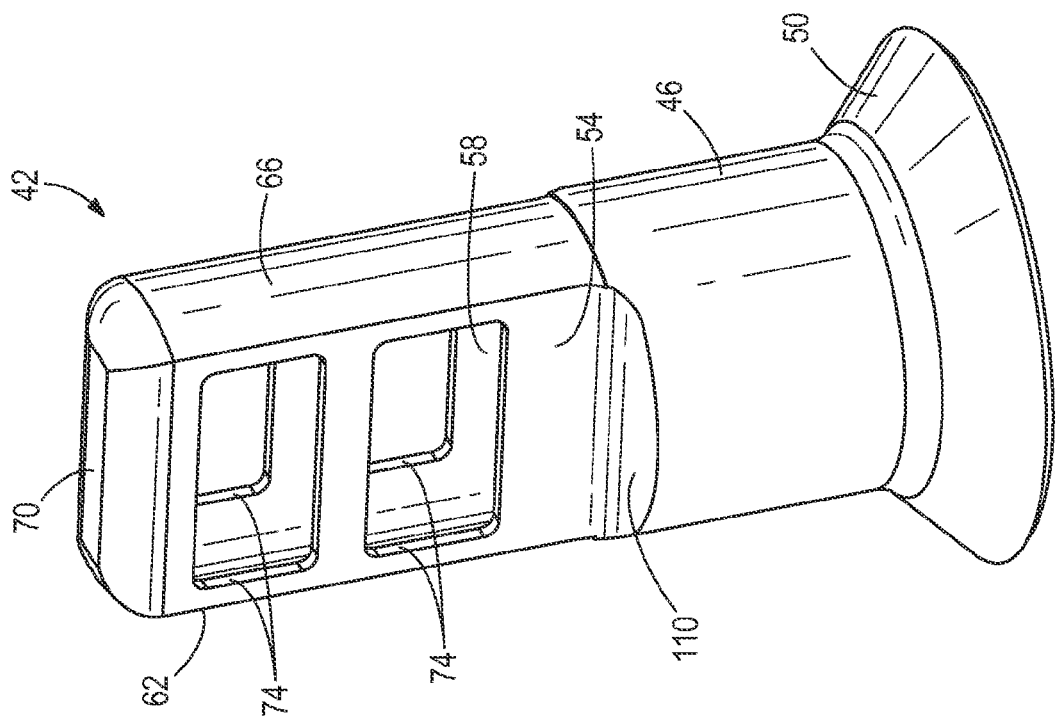

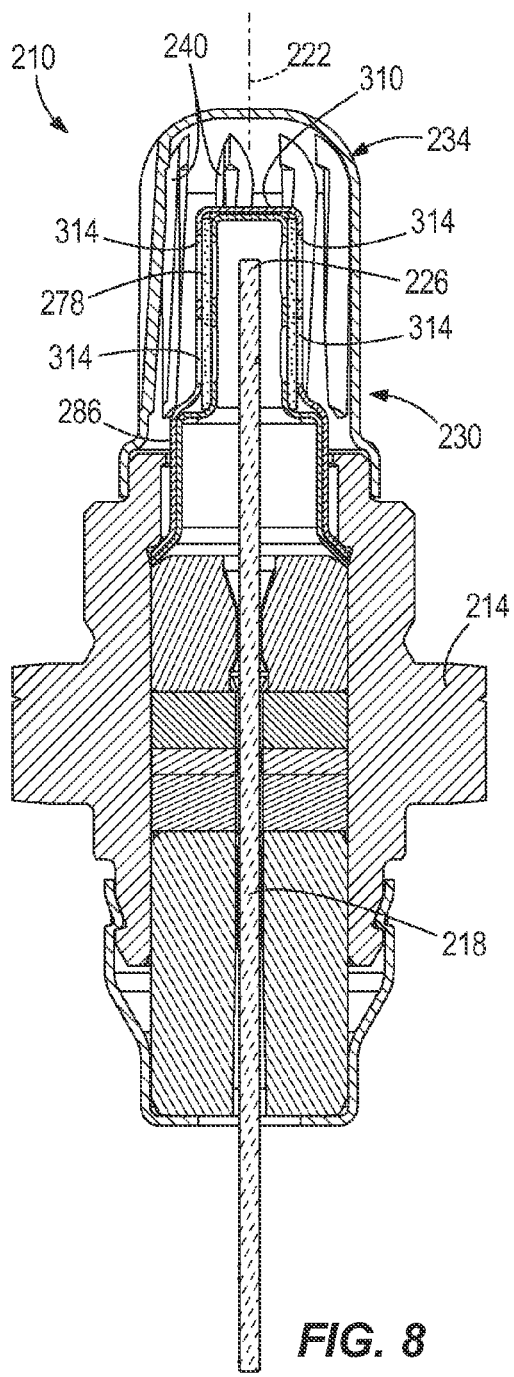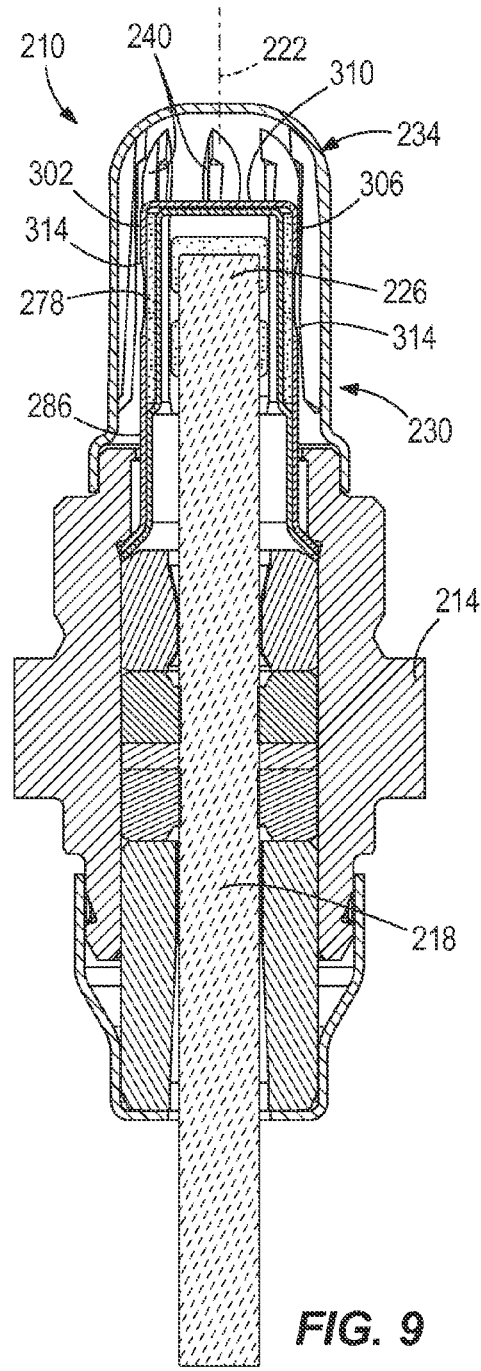
FIG. 8
FIG. 9

GAS SENSOR WITH THERMAL SHOCK PROTECTION

CROSS REFERENCE TO RELATED APPLICATIONS

This application claims priority to U.S. Provisional Application No. 61/740,199, filed Dec. 20, 2012, the entire contents of which are incorporated herein by reference.

BACKGROUND

The present invention relates to a gas sensor, and more particularly to a gas sensor with a sensor protection element that protects against thermal shock.

The use of gas sensors to monitor oxygen levels in an internal combustion engine is known. Current gas sensors are designed for use in the exhaust manifold, where the sensors detect a lean/rich operating condition of the engine, based on the exhaust gas, and communicate with an engine control unit to manage performance of the engine. The gas sensors include ceramic sensing elements extending from sensor housings for detecting the oxygen levels of the exhaust gas.

At engine start-up, before the exhaust gas heats up to operating temperature, water often exists in the exhaust passage. Because the ceramic sensing elements are heated to very high temperatures for operation, the ceramic sensing elements are susceptible to damage (e.g., cracking) in the event that liquid water contacts the sensing elements. Thus, it may be necessary to delay the operation of the gas sensor until the exhaust gas has heated up sufficiently to eliminate most or all of the liquid water.

One known solution to this problem is disclosed in U.S. patent application Ser. No. 12/130,701, published as U.S. 2009/0101502 and incorporated by reference herein, which provides a plasma-sprayed gamma alumina coating over the sensing element. Although this process has proven to be effective for protecting ceramic sensor elements from thermal shock at temperatures up to about 750 degrees Celsius, the plasma spraying process itself presents inherent cost and risk of sensor damage. Further advances in thermal shock protection and manufacturing cost reductions are desired

SUMMARY

In accordance with one construction, a gas sensor includes a sensor housing, a sensing element located within the sensor housing, the sensing element defining an axis and having a distal end extending from the sensor housing, and a sensor protection element coupled to the sensor housing and at least partially surrounding the distal end of the sensing element. The sensor protection element includes a tube, the distal end of the sensing element located within the tube, the tube including a window located on a side of the tube adjacent the distal end of the sensing element, and a fabric layer positioned adjacent the window, the fabric layer spaced from the sensing element and extending generally parallel to the axis.

In accordance with another construction, a gas sensor includes a sensor housing, a sensing element located within the sensor housing, the sensing element defining an axis and having a distal end extending from the sensor housing, and a sensor protection element coupled to the sensor housing and at least partially surrounding the distal end of the sensing element. The sensor protection element includes an inner tube. The distal end of the sensing element is located within the inner tube. The inner tube includes a window located along a side of the inner tube adjacent the distal end of the sensing element. A fabric layer is positioned adjacent the window. The fabric layer is spaced from the sensing element and extends generally parallel to the axis. An outer tube at least partially surrounds the inner tube, and an intermediate tube is positioned between the outer tube and the inner tube.

BRIEF DESCRIPTION OF THE DRAWINGS

FIG. 3 a perspective view of an inner tube portion of the sensor protection element of FIG. 1.

FIG. 4 is a perspective view of a fabric layer of the sensor protection element of FIG. 1.

FIG. 5 is a perspective view of a retainer portion of the sensor protection element of FIG. 1

FIG. 8 is a front cross-sectional view of a gas sensor according to another construction of the invention, the gas sensor including a sensor protection element.

FIG. 9 is a right side cross-sectional view of the gas sensor of FIG. 8.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
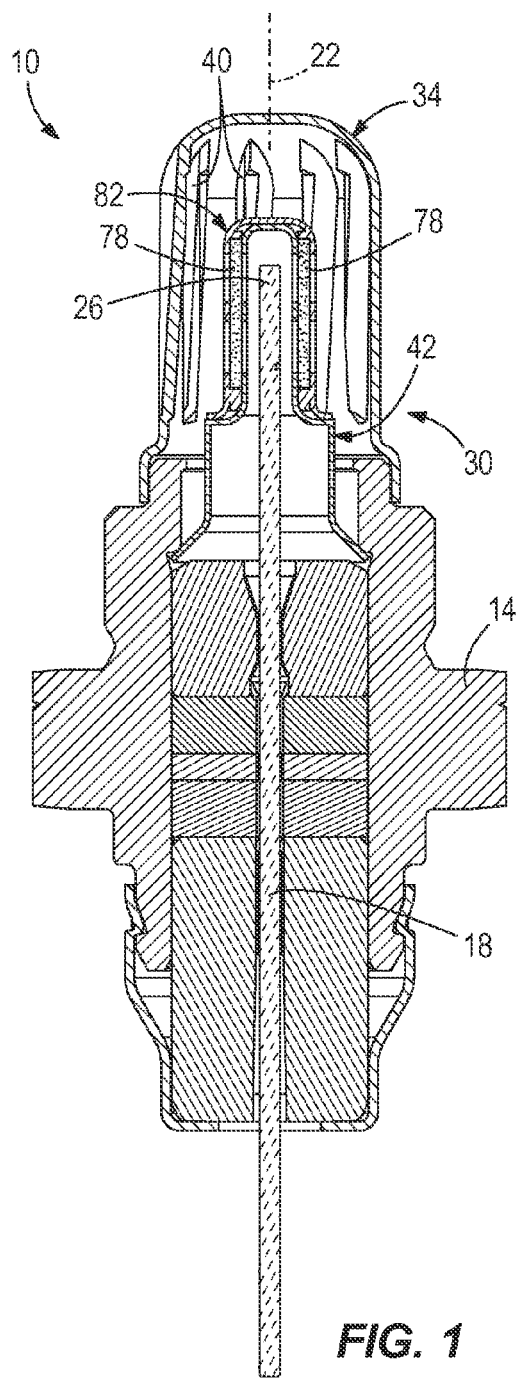
FIG. 1 is a front cross-sectional view of a gas sensor according to one construction of the invention, the gas sensor including a sensor protection element.
Figure 2:
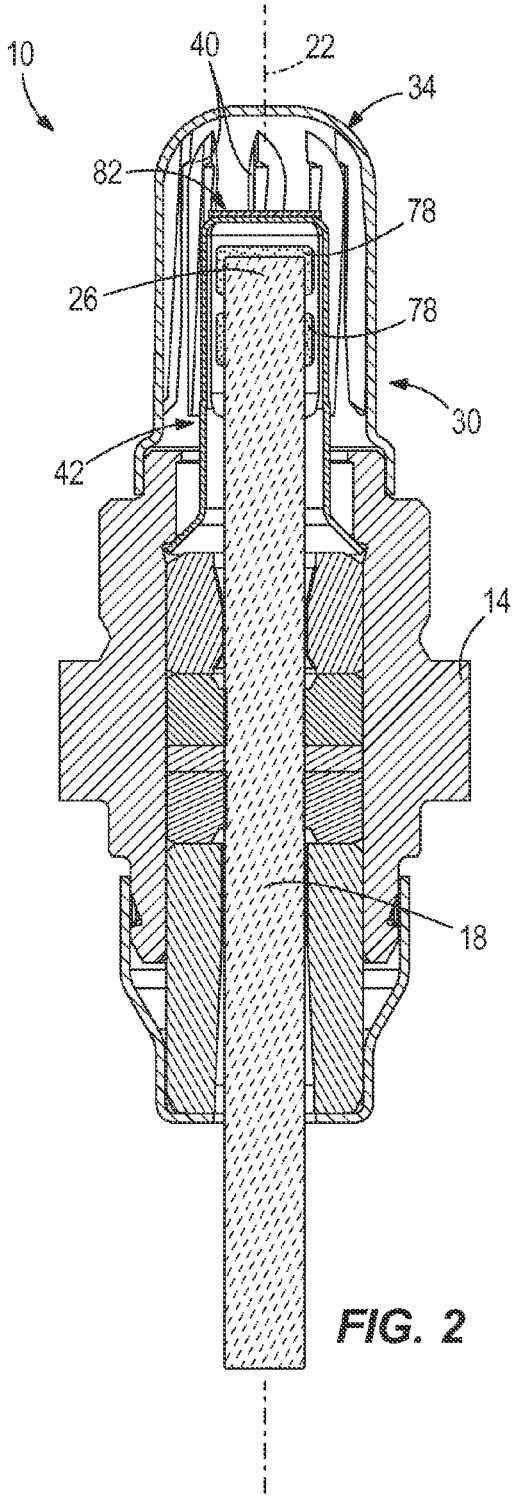
FIG. 2 is a right side cross-sectional view of the gas sensor of FIG. 1.

FIGS. 1 and 2 illustrate a gas sensor 10. The gas sensor 10 includes a sensor housing 14, and a sensing element 18 located within the sensor housing 14. The sensing element 18 is an oxygen sensing element, although other types of sensing elements 18 are also possible. The sensing element 18 defines an axis 22. The sensing element 18 has a distal end 26 extending from the sensor housing 14. The distal end 26 extends along the axis 22.

The gas sensor 10 further includes a sensor protection element 30. The sensor protection element 30 is coupled to the sensor housing 14. Specifically, the sensor protection element 30 is coupled to the sensor housing 14 via a frictional fit over the housing 14, although other forms of coupling are also possible, including attachment with fasteners, brazing, welding, etc. The sensor protection element 30 at least partially surrounds the distal end 26 of the sensing element 18. The sensor protection element 30 controls the flow of gas from outside the sensor protection element 30, into communication with the sensing element 18, and back outside the sensor protection element 30.

The sensor protection element 30 includes an outer tube 34 that at least partially surrounds the distal end 26 of the sensing element 18. The outer tube 34 includes gas inlets and outlets 40 that permit gas to enter and exit through the outer tube 34. In some embodiments an intermediate tube is also present, disposed at least partially within the outer tube 34.

The sensor protection element 30 further includes an inner tube 42. As illustrated in FIG. 3, the inner tube 42 includes a cylindrical base portion 46, a flange portion 50 extending below the cylindrical portion 46, a first generally planar surface 54 extending above the cylindrical base portion 46, a second generally planar surface 58 located opposite the first generally planar surface 54 and extending above the cylindrical base portion 46, a first curved end portion 62 located between the first and second generally planar surfaces 54, 58, a second curved end portion 66 located between the first and second generally planar surfaces 54, 58 and opposite the first curved end portion 62, a top portion 70 extending between the first curved end portion 62 and second curved end portion 66, and a plurality of windows 74 located on the first and second generally planar surfaces 54, 58. The inner tube 42 is coupled to the sensor housing 14. Specifically, the inner tube 42 is coupled to the sensor housing 14 via a frictional fit with the flange portion 50 over the housing 14, although other forms of coupling are also possible, including attachment with fasteners, brazing, welding, etc. The inner tube 42 at least partially surrounds the distal end 26 of the sensing element 18 and is made of stainless steel, though other types of material are also possible.

The sensor protection element 30 further includes a plurality of fabric layers 78. As illustrated in FIG. 4, the each fabric layer 78 is pre-formed as a panel of braided fabric, and has a generally rectangular shape, although other shapes are also possible, including trapezoidal or circular shapes. In some constructions the fabric panel is not braided, but is woven, knitted, etc. The fabric layers 78 are made of Nextel™ 312 fabric, although other types of fabric are also possible, including a metal oxide ceramic fiber material, such as refractory aluminoborosilicate, aluminosilica, or alumina. Examples of commercially available materials are 3M™ NEXTEL™ variety "312". 3M™ NEXTEL™ 312 is made up of 62.5 percent $Al_2O_3$, 24.5 percent $SiO_2$, and 13 percent $B_2O_3$. In some constructions the fabric layers 78 are sewing thread (e.g. reinforced with 5 wt. percent rayon to improve processability), or roving. Overall, the fabric layers 78 permit gas to pass through the fabric layers 78, but inhibit water, particles, and/or other contaminates from passing through the fabric layers 78. While various types of fabric can be used, it has been found that sewing thread as a type of fabric for fabric layer 78 may be more robust in the manufacturing process than other types of fabric for the fabric layers 74. The rayon cleanly and completely burns out at 300 degrees Celsius.

The sensor protection element 30 further includes a retainer element 82. As illustrated in FIG. 5, the retainer element 82 includes a top portion 86, a first generally planar surface 90 extending below the top portion 86, a second generally planar surface 94 extending below the top portion 86 and located opposite the first generally planar surface 90, a first flange 98 extending away from the first generally planar surface 86, a second flange 102 extending away from the second generally planar surface 90, and a plurality of windows 106 located on the first and second generally planar surfaces 90, 94.

Figure 7:
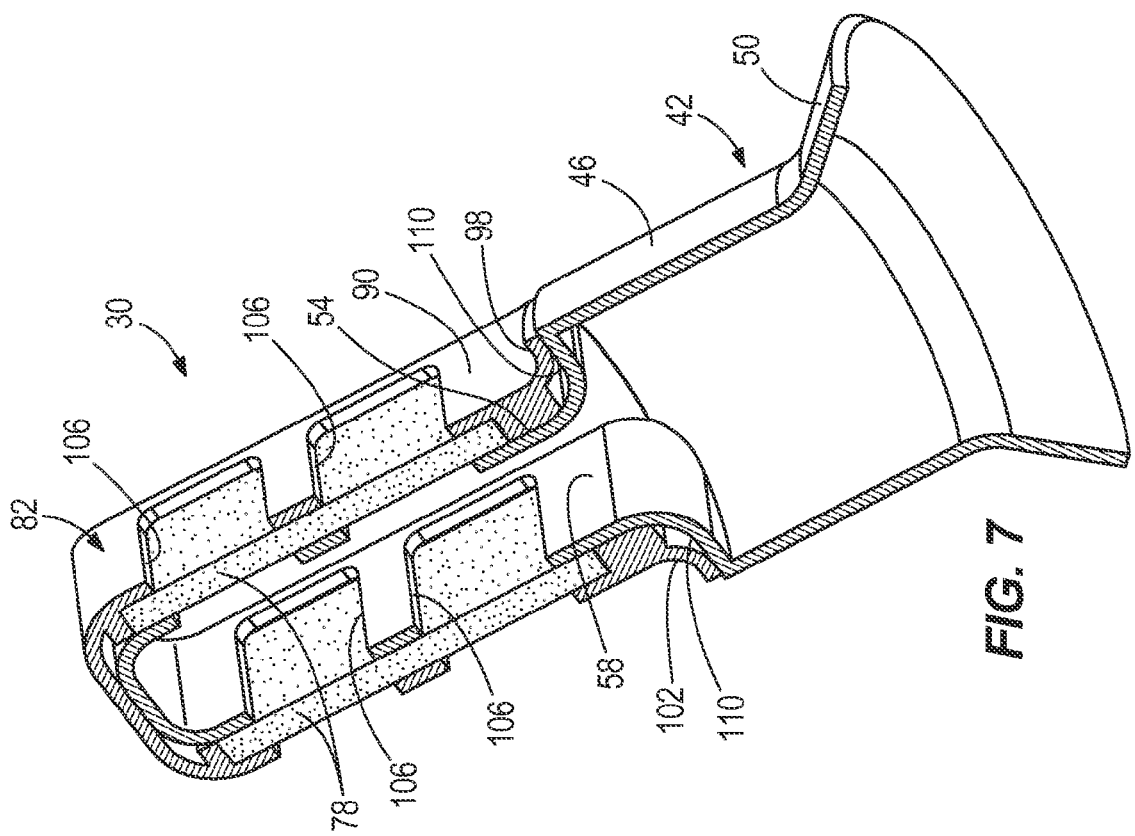
FIG. 7 is a cross-sectional view of a portion of the sensor protection element of FIG. 1.
Figure 6:
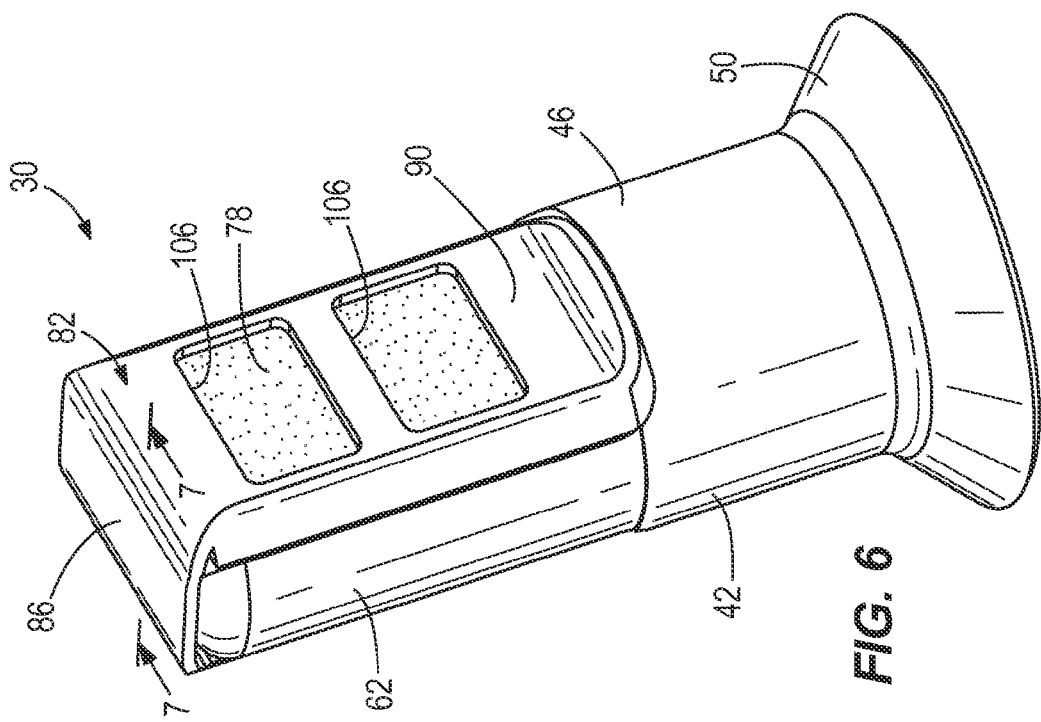
FIG. 6 is a perspective view of a portion of the sensor protection element of FIG. 1.

With reference to FIGS. 6 and 7, the retainer element 82 has a generally U-shaped, or stirrup-shaped profile. The profile of the retainer element 82 closely resembles the profile of the inner tube 42. Specifically, the profile formed by the top portion 86, first generally planar surface 90, and second generally planar surface 94 of the retainer element 82 is similar to the profile formed by the top portion 70, first generally planar surface 54, and second generally planar surface 58 of the inner tube 42, such that the retainer element 82 fits much like a sleeve over the inner tube 42.

With continued reference to FIGS. 6 and 7, the fabric layers 78 are disposed between the inner tube 42 and the retainer element 82. The fabric layers 78 are disposed across the windows 74 of the inner tube 42 and the windows 106 of the retainer element 82, such that one fabric layer 78 extends across two windows 74, 106 on one side of the sensor protection element 30, and another fabric layer 78 extends across two windows 74, 106 on the other side of the sensor protection element 30. Four windows 74, four windows 106, and two fabric layers 74 in total are illustrated. However, in other constructions various other numbers of windows 70 and fabric layers 74 are used. When the sensor protection element 30 is assembled, each of the fabric layers 74 extends generally parallel to the axis 22, and alongside the sensing element 18.

With continued reference to FIG. 7, the retainer element 82 is coupled to the inner tube 42. Specifically, the retainer element 82 is coupled to the inner tube 42 via a frictional fit (e.g. via a pressing process), although other forms of coupling are also possible, including attachment with fasteners, brazing, welding, etc. When the retainer element 82 is coupled to the inner tube 42, the first and second flanges 98, 102 align with and/or contact an annular shoulder 110 located along a top of the cylindrical portion 46 of the inner tube 42. The retainer element 82 and the inner tube 42 are spaced apart slightly between the first and second generally planar surfaces 90, 94 of the retainer element 82 and the first and second generally planar surfaces 54, 58 of the inner tube 42, so as to provide room for the fabric layers 78. When coupled together with the inner tube 42, the retainer element 82 presses against the fabric layers 78, thereby holding the fabric layers 78 in position across the windows 74, 106.

As noted above, the fabric layers 78 permit gas to pass through, but not water, particles, or other contaminants. Thus, the combination of the inner tube 42, retainer element 82, and fabric layers 78 allows gas to pass from within the outer tube 34 into the inner tube 42, where the gas contacts the sensing element 18 and then passes back out of the inner tube 42 and into the outer tube 34. The inner tube 42, fabric layers 78, and retainer element 82 inhibit or prevent water, particles, or other contaminants from contacting the sensing element 18.

The sensing element 18, which is typically ceramic, reaches high temperature levels during operation. The fabric layers 78 are positioned close enough to the sensing element 18 that the fabric layers 78 become hot enough to evaporate water particles that contact the fabric layers 78, but are also spaced apart from the sensing element 18 at all locations of the fabric layers 78. If the fabric layers 78 were to contact the sensing element at any point, a capillary action could occur, in which a water droplet works its way down the fabric layer 78 to the location where the fabric layer 78 contacts the sensing element 18. If the water droplet has not yet evaporated, contact between the water droplet and the sensing element 18 could cause thermal shock to the sensing element 18, and damage the sensing element 18. Therefore, the fabric layers 78 are arranged between the inner tube 42 and retainer element 82 such that the fabric layers 74 run generally parallel to the axis 22 and are in close proximity to the sensing element 18, but are spaced by a gap at all points between the fabric layers 78 and the sensing element 18.

FIGS. 8 and 9 illustrate a gas sensor 210 in accordance with another construction. The gas sensor 210 includes a sensor housing 214, and a sensing element 218 located within the sensor housing 214. The sensing element 218 is an oxygen sensing element, although other types of sensing elements 218 are also possible. The sensing element 218 defines an axis 222. The sensing element 218 has a distal end 226 extending from the sensor housing 214. The distal end 226 extends along the axis 222.

The gas sensor 210 further includes a sensor protection element 230. The sensor protection element 230 is coupled to the sensor housing 214. Specifically, the sensor protection element 230 is coupled to the sensor housing 214 via a frictional fit over the housing 214, although other forms of coupling are also possible, including attachment with fasteners, brazing, welding, etc. The sensor protection element 230 at least partially surrounds the distal end 226 of the sensing element 218. The sensor protection element 230 controls the flow of gas from outside the sensor protection element 230, into communication with the sensing element 218, and back outside the sensor protection element 230.

The sensor protection element 230 includes an outer tube 234 that at least partially surrounds the distal end 226 of the sensing element 218. The outer tube 234 includes gas inlets and outlets 240 that permit gas to enter and exit through the outer tube 234. In some embodiments an intermediate tube is also present, disposed at least partially within the outer tube 234.

Figure 10:
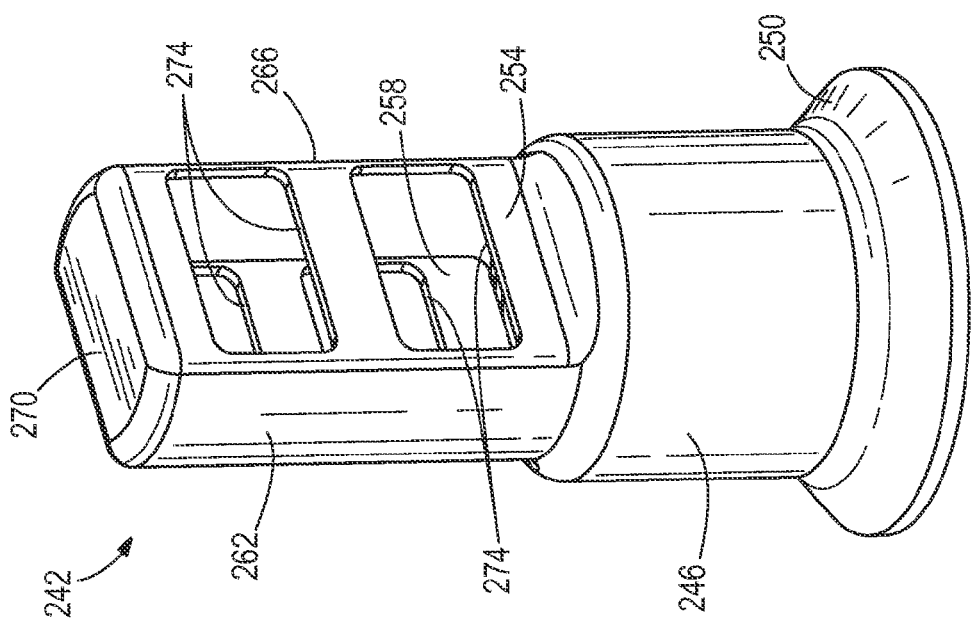
FIG. 10 a perspective view of an inner tube portion of the sensor protection element of FIG. 8.

The sensor protection element 230 further includes an inner tube 242. As illustrated in FIG. 10, the inner tube 242 includes a cylindrical base portion 246, a flange portion 250 extending below the cylindrical portion 246, a first generally planar surface 254 extending above the cylindrical base portion 246, a second generally planar surface 258 located opposite the first generally planar surface 254 and extending above the cylindrical base portion 246, a first curved end portion 262 located between the first and second generally planar surfaces 254, 258, a second curved end portion 266 located between the first and second generally planar surfaces 254, 258 and opposite the first curved end portion 262, a top portion 270 extending between the first curved end portion 262 and second curved end portion 266, and a plurality of windows 274 located on the first and second generally planar surfaces 254, 258. The inner tube 242 is coupled to the sensor housing 214. Specifically, the inner tube 242 is coupled to the sensor housing 214 via a frictional fit with the flange portion 250 over the housing 214, although other forms of coupling are also possible, including attachment with fasteners, brazing, welding, etc. The inner tube 242 at least partially surrounds the distal end 226 of the sensing element 218 and is made of stainless steel, though other types of material are also possible.

Figure 11:
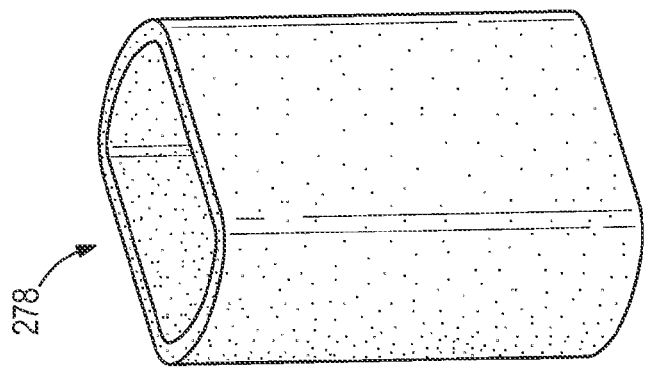
FIG. 11 is a perspective view of a fabric layer of the sensor protection element of FIG. 8.

The sensor protection element 230 further includes a fabric layer 278. As illustrated in FIG. 11, the fabric layer 278 is in the form of a tube. The fabric layer 278 is made of Nextel™ 312 fabric, although other types of fabric are also possible, including a metal oxide ceramic fiber material, such as refractory aluminoborosilicate, aluminosilica, or alumina. Examples of commercially available materials are 3M™ NEXTEL™ variety "312". 3M™ NEXTEL™ 312 is made up of 62.5 percent $Al_2O_3$, 24.5 percent $SiO_2$, and 13 percent $B_2O_3$. In other constructions the fabric layer 278 is sewing thread (e.g. reinforced with 5 wt. percent rayon to improve processability), or roving. While various types of fabric can be used, it has been found that sewing thread as a type of fabric for fabric layer 278 may be more robust to handling in the manufacturing process than other types of fabric for the fabric layer 278. Rayon cleanly and completely burns out at 300 degrees Celsius.

To form the fabric layer 278, a string of fabric is wrapped multiple times around the inner tube 242 during manufacturing, such that a layer (or layers) of fabric material are formed over the windows 274. The formed fabric layer 278 permits gas to pass through the fabric layer 278, but inhibit water, particles, and/or other contaminates from passing through the fabric layer 278. In an assembled state, the fabric layer 278 is disposed across the windows 274, such that the fabric layer 278 covers each of the four windows 274.

Figure 12:
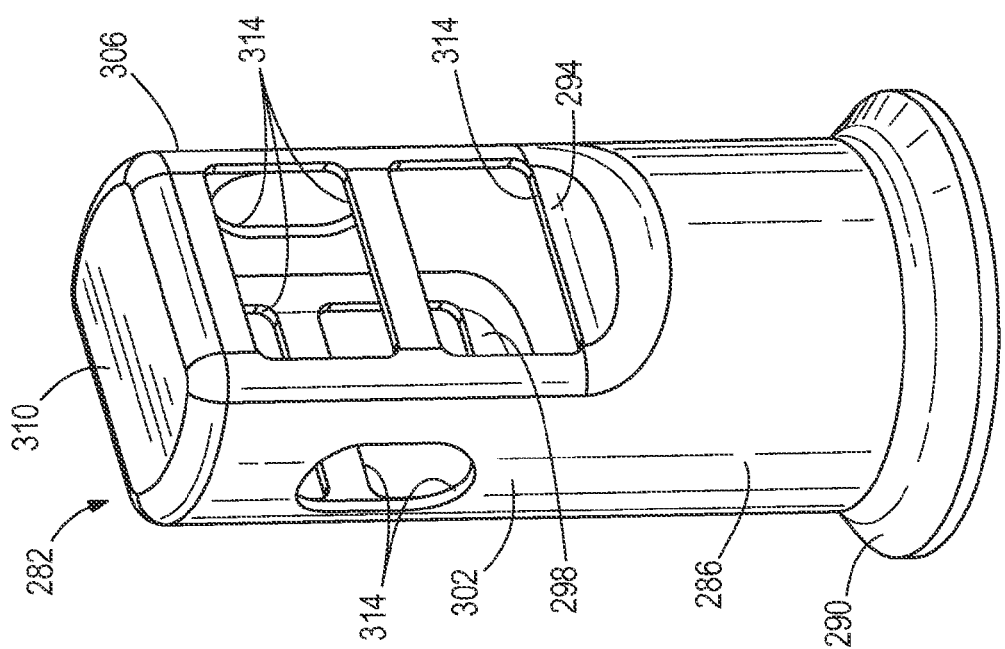
FIG. 12 is a perspective view of a retainer portion of the sensor protection element of FIG. 8.

The sensor protection element 230 further includes a retainer element 282. As illustrated in FIG. 12, the retainer element 282 includes a cylindrical base portion 286, a flange portion 290 extending below the cylindrical base portion 286, a first generally planar surface 294 extending above the cylindrical base portion 286, a second generally planar surface 298 located opposite the first generally planar surface 294 and extending above the cylindrical base portion 286, a first curved end portion 302 located between the first and second generally planar surfaces 294, 298, a second curved end portion 306 located between the first and second generally planar surfaces 294, 298 and opposite the first curved end portion 302, a top portion 310 extending between the first curved end portion 302 and second curved end portion 306, and a plurality of windows 314 located on the first and second generally planar surfaces 294, 298 and the curved end portions 302, 306.

Figures 13, 14:
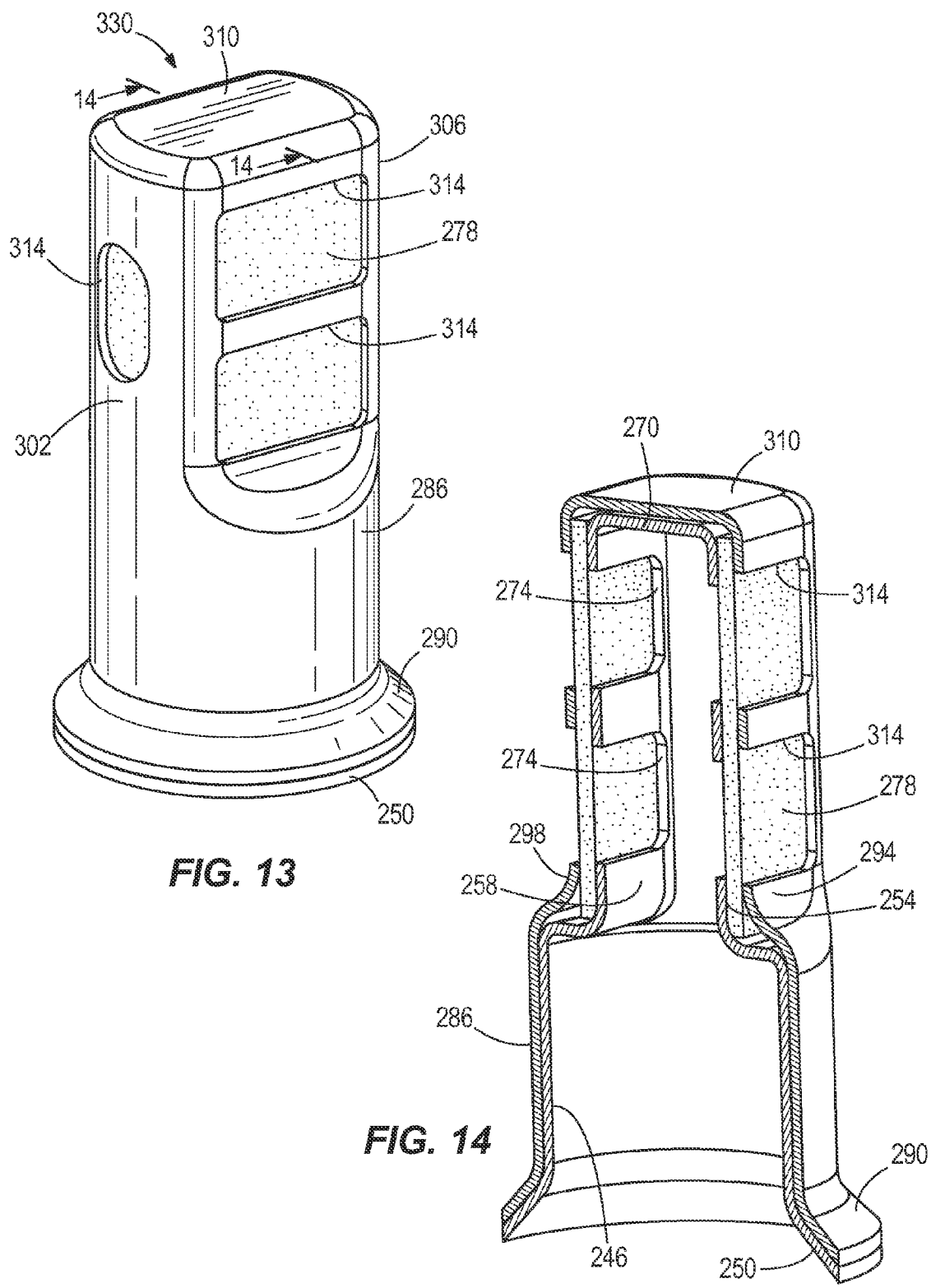
FIG. 13 is a perspective view of a portion of the sensor protection element of FIG. 8.
FIG. 14 is a cross-sectional view of a portion of the sensor protection element of FIG. 8.

With reference to FIGS. 13 and 14, the retainer element 282 is coupled to the inner tube 242. Specifically, the retainer element 282 is coupled to the inner tube 242 via a frictional fit, although other forms of coupling are also possible, including attachment with fasteners, brazing, welding, etc. When the retainer element 282 is coupled to the inner tube 242, the flange portions 290, 250 align with and/or contact each other. Additionally, the windows 314 on the first and second planar surfaces 294, 298 of the retainer element 282 align with the windows 274 on the planar surfaces 254, 258 of the inner tube 242. The windows 314 on the curved end portions 302, 306 do not align with any windows on the inner tube 242. The function of these windows 314 will be disclosed below.

The retainer element 282 and the inner tube 242 are spaced apart slightly so as to provide room for the fabric layer 278. When coupled together with the inner tube 242, the retainer element 282 presses against the fabric layer 278, thereby holding the fabric layer 278 in position across the windows 274 of the inner tube 242.

The combination of the inner tube 242, retainer element 282, and fabric layer 278 allows gas to pass from within the outer tube 234 into the inner tube 242, where the gas contacts the sensing element 218 and then passes back out of the inner tube 242 and into the outer tuber 234. The inner tube 242, fabric layer 278, and retainer element 282 inhibit or prevent water, particles, or other contaminants from contacting the sensing element 218.

Additionally, the fabric layer 278 is arranged between the inner tube 242 and the retainer element 282 such that the fabric layer 278 run generally parallel to the axis 222 and is in close proximity to the sensing element 218, but wherein a gap is maintained at all points between the fabric layer 78 and the sensing element 218.

As illustrated in FIGS. 12-13, the windows 314 on the curved end portions 302, 306 of the retainer element 282 have a generally elliptical shape, and the windows 314 on the first and second generally planar surfaces 294, 298 have a generally rectangular shape. Other shapes and/or sizes for the windows 314 are also possible. In some constructions the windows 314 each have the same general shape.

The windows 314 on the curved end portions 302, 306 provide a pathway for water to contact the heated fabric layer 278, without providing any further opening along the inner tube 242 for the possible water, particles, and/or other contaminants to travel into the inner tube 242. In this manner, the portions of the fabric layer 278 that are exposed along the curved end portions 302, 306 of the retainer element 282 provide areas solely dedicated to water evaporation. While such areas are illustrated only as being on the curved end portions 302, 306, in other constructions windows 314 are provided elsewhere along the retainer element 282 to provide access to the fabric layer 278.

While the various constructions illustrated in FIGS. 1-12 include a separate retainer element 82, 282 positioned over an inner tube 42, 242, in other constructions a sensor protection element 30, 230 includes multiple retainer elements 82, 282 of various sizes and shapes. In yet further constructions the sensor protection element 30, 230 includes a retainer element 82, 282 that is formed integrally with the inner tube 42, 242, or that is resistance or laser welded to the inner tube 42, 242, or that does not couple with the inner tube 42, 242 at all. In some constructions the sensor protection element 30, 230 includes no retainer elements 82, 282. Rather, the fabric layer 78, 278 is held in place by the inner tube 42, 242 itself.

Thermal shock measurements using an ENG standard thermal shock tester were taken to evaluate the effectiveness of the wound fabric layer 278 described above. Various materials for the fabric layer 278 were tested, including sewing thread, 600 denier yarn—single layer, and 600 denier yarn—double layer. The test involved applying 10 µl water drops to the fabric layer 278 when the sensing element 218 temperature was as high as 900 degrees Celsius.

In the ENG thermal shock tester a FLIR IR camera was initially used to measure sensing element 218 surface temperature. This did not report the correct temperature when looking at Nextel™ fabric. Therefore, the sensing element 218 temperature was estimated from the applied heater power.

The detailed results of the testing are provided below:

| Design | Fabric Weight | Thermal Shock |
|---|---|---|
| Sewing Thread | 0.1 gr. | Pass 900 C. |
| 600 denier yarn | 0.1 gr. | Pass 900 C. |
| 600 denier yarn (2 layers) | 0.2 gr. | Pass 900 C. |

As indicated in the results, thermal shock resistance with the spaced fabric layers 278 passed the thermal shock test of 900 degrees Celsius, and was at least 100 degrees Celsius better than results obtained with a conventional gas sensor having a plasma sprayed alumina coating. With a manually wound fabric layer 278, no thermal shock was observed with 10 µl water drops applied to the fabric layer 278 when the sensing element 218 temperature was as high as 900 degrees Celsius. The spaced fabric layer 278 design was therefore found to be robust to at least 900 degrees Celsius. With this robust design, a sensor heater (which heats the sensing element 218) is able to be powered on immediately when a car is started, without the risk of thermal shock from liquid water in the exhaust pipe. This allows improved closed loop engine control, and reduces emissions.

Additionally, using an inner tube 42, 242 reduces fabric cost. Specifically, it is expected that the amount of fabric for the fabric layers 78, 278 required to ensure thermal shock resistance will have at least a 50 percent lower cost than for example using only a woven sleeve extending over the sensing element 18, 218 (i.e. a layer of fabric, in the form of a sleeve, positioned to extend over the sensing element 18, without the use of an inner tube 42, 242).

Also, during manufacturing, winding the fabric layer 278 over the inner tube 242, or forming a fabric layer 78 in the form of a panel, is able to be performed independently of pre-assembly for the gas sensor 10. In this manner all types of gas sensors (e.g. Bosch LSF, LSU 4.x, LSU5.x, Xfour) are able to be assembled on existing assembly lines. The only modification required is to align the sensing element 18, 218 with the inner tube 42, 242. Thus, the pre-assembly process requires no modification from a standard series process which has been used for several years, thereby eliminating capital costs for new equipment.

Various features and advantages of the invention are set forth in the following claims.

What is claimed is:

1. A gas sensor comprising:
a sensor housing;
a sensing element located within the sensor housing, the sensing element defining an axis and having a distal end extending from the sensor housing; and
a sensor protection element coupled to the sensor housing and at least partially surrounding the distal end of the sensing element, the sensor protection element including:
an inner tube, the distal end of the sensing element located within the inner tube, the inner tube including a general planar surface, and a window located on the generally planar surface adjacent the distal end of the sensing element;
a retainer element positioned over the inner tube; and
a fabric layer positioned adjacent the window, the fabric layer spaced from the sensing element and extending generally parallel to the axis.

2. The gas sensor of claim 1, wherein the fabric layer is spaced from the sensing element at all locations of the fabric layer.

3. The gas sensor of claim 1, wherein the inner tube includes a plurality of windows, the fabric layer positioned adjacent each of the plurality of windows.

4. The gas sensor of claim 1, wherein the fabric layer is a fabric panel positioned adjacent the window.

5. The gas sensor of claim 1, wherein the fabric layer is a layer of fabric wound around the inner tube and over the window.

6. The gas sensor of claim 1, wherein the fabric layer is made from a ceramic fabric thread or yarn.

7. The gas sensor of claim 1, wherein the inner tube includes a generally cylindrical base portion with a flange at one end of the base portion.

8. The gas sensor of claim 1, wherein the inner tube includes four windows and two generally planar surfaces, two of the four windows located on one of the two generally planar surfaces, and the other two windows located on the other of the two planar surfaces.

9. The gas sensor of claim 8, wherein the inner tube includes curved portions extending between the two generally planar surfaces.

10. The gas sensor of claim 1, wherein the fabric layer is generally rectangular in shape.

11. The gas sensor of claim 1, wherein the fabric layer is positioned between the inner tube and the retainer element.

12. The gas sensor of claim 1, wherein the retainer element is coupled to the inner tube.

13. A gas sensor comprising:
a sensor housing;
a sensing element located within the sensor housing, the sensing element defining an axis and having a distal end extending from the sensor housing; and
a sensor protection element coupled to the sensor housing and at least partially surrounding the distal end of the sensing element, the sensor protection element including:
- an inner tube, the distal end of the sensing element located within the inner tube, the inner tube including a window located along a side of the inner tube adjacent the distal end of the sensing element;
- a fabric layer positioned adjacent the window, the fabric layer spaced from the sensing element and extending generally parallel to the axis;
- a retainer element positioned over and at least partially surrounding the inner tube, such that at least a portion of the fabric layer is disposed between the inner tube and the retainer element; and
- an outer tube at least partially surrounding both the inner tube and the retainer element.

14. The gas sensor of claim 13, wherein the fabric layer is spaced from the sensing element at all locations of the fabric layer.

15. The gas sensor of claim 13, wherein the fabric layer is one of a fabric panel and a fabric tube.

16. The gas sensor of claim 13, wherein at least a portion of the outer tube is spaced from the retainer element.

17. The gas sensor of claim 13, wherein the outer tube includes a gas inlet and a gas outlet.

18. A gas sensor comprising:
a sensor housing;
a sensing element located within the sensor housing, the sensing element defining an axis and having a distal end extending from the sensor housing; and
a sensor protection element coupled to the sensor housing and at least partially surrounding the distal end of the sensing element, the sensor protection element including:
- an inner tube, the distal end of the sensing element located within the inner tube, the inner tube including a first window located along a side of the inner tube adjacent the distal end of the sensing element;
- a fabric layer positioned adjacent the first window, the fabric layer spaced from the sensing element and extending generally parallel to the axis; and
- a retainer element at least partially surrounding the inner tube and the fabric layer, the retainer element including a second window aligned with the first window along a direction perpendicular to the axis such that a first portion of the fabric layer is disposed between the first and second windows, and wherein the retainer element includes a third window not aligned with any windows on the inner tube along a direction perpendicular to the axis, such that a second portion of the fabric layer is disposed between the third window and a solid portion of the inner tube.

19. The gas sensor of claim 18, wherein the inner tube and the retainer each include a generally planar surface, and wherein the first and the second windows are each disposed on one of the generally planar surfaces.

* * * * *